(12) United States Patent
Smith et al.

(10) Patent No.: US 6,827,936 B1
(45) Date of Patent: Dec. 7, 2004

(54) SYNTHETIC PEPTIDE VACCINES FOR DENTAL CARIES

(75) Inventors: Daniel J. Smith, Natick, MA (US); Martin A. Taubman, Newtonville, MA (US)

(73) Assignee: Forsyth Dental Infirmary for Children, Boston, MA (US)

(*) Notice: Subject to any disclaimer, the term of this patent is extended or adjusted under 35 U.S.C. 154(b) by 0 days.

(21) Appl. No.: 09/290,049

(22) Filed: Apr. 12, 1999

Related U.S. Application Data

(60) Provisional application No. 60/115,142, filed on Jan. 8, 1999, and provisional application No. 60/081,550, filed on Apr. 13, 1998.

(51) Int. Cl.$^7$ .................. A61K 39/02; A61K 39/38; A61K 38/00; C07H 21/04
(52) U.S. Cl. .................. 424/190.1; 424/9.1; 424/9.2; 424/184.1; 424/185.1; 424/193.1; 424/197.11; 424/203.1; 424/234.1; 424/244.1; 435/69.1; 435/183; 435/193; 435/253.4; 530/300; 530/350; 536/23.1; 536/23.7
(58) Field of Search .................. 424/190.1, 197.11, 424/203.1, 9.1, 9.2, 184.1, 185.1, 193.1, 234.1, 244.1; 530/350, 324, 300; 536/23.1, 23.7; 435/69.1, 183, 193, 253.4

(56) References Cited

U.S. PATENT DOCUMENTS

| | | | |
|---|---|---|---|
| 4,150,116 A | 4/1979 | Taubman et al. | 424/88 |
| 4,250,262 A | 2/1981 | Taubman et al. | 435/193 |
| 4,438,200 A | 3/1984 | Taubman et al. | 435/193 |
| 5,686,075 A | 11/1997 | Taubman et al. | |

FOREIGN PATENT DOCUMENTS

WO    WO 99/07828    2/1999

OTHER PUBLICATIONS

Kuramitsu, H. K., et al., "Antigenic relationships between the glucosyltransferase activity of Streptococcus mutans suspecies mutans", Archives of Oral Biology, Vol. 23, No. 8, pages 691–696, 1978.*

Shiroza et al. J Bacteriol 169: 4263–4270.*

Taubman M. A., and D. J. Smith, Effects of Local Immunization with Glucosyltransferase Fractions From *Streptococcus mutans* on Dental Caries in Rats and Hamsters, *J. Immunology*, 118(2):710–720 (1977).

Smith, D. J., et al., "Effects of Local Immunization with Glucosyltransferase Fractions from *Streptococcus mutants* on Dental Caries in Hamsters Caused by Homologous and Heterologous Serotypes of *Streptococcus mutants*," *Infect. Immun.* 21(3):843–851 (1978).

Smith, D. J., et al., "Preparation of Glucosyltransferase from *Streptococcus mutans* by Elution from Water–Insoluble Polysaccharide with a Dissociating Solvent," *Infect. Immunity*, 23(2):446–452 (1979).

Smith, D. J., et al., Effect of Oral Administration of Glucosyltransferase Antigens on Experimental Dental Caries, *Infection Immunity*, 26(1):82–89 (1979).

Smith, D. J., et al., "Local and Systemic Antibody Response to Oral Administration of Glucosyltransferase Antigen Complex," *Infection Immunity*, 28(2):441–450 (1980).

Smith, D. J., et al., "Effects of Local Immunization with Glucosyltransferase on Colonization of Hamsters by *Streptococcus mutans*," *Infection Immunity*, 37(2):656–661 (1982).

Smith, D. J., et al., "Effects of Local Immunization of Hamster with Glucosyltransferase Antigens on Infection with *Streptococcus sanguis*," *Infect. Immunity*, 42(1):156–162 (1983).

Taubman, M. A., et al., "Immunological Interference with Accumulation of Cariogenic Microorganisms on Tooth Surfaces," in *Recent Advances in Mucosal Immunity*, W. Strober, et al., eds. (NY: Raven Press) pp. 371–382 (1982).

Taubman, M. A., et al., "Protective Aspects of Immune Response to Glucosyltransferase in Relation to Dental Caries," in *Glucosyltransferase, Glucans, Sucrose and Dental Caries*, R. Doyle and J. E. Ciardi, eds., Sp. Supp., *Chemical Senses*, pp. 249–258 (1983).

Smith, D. J., et al., "Effect of Antibody in Gingival Crevicular Fluid on Early Colonization of Exposed Root Surfaces by Mutans Streptococci," *Oral. Micro. Immunol.*, 9:65–69 (1994).

Smith, D. J. and M. A. Taubman, "Effect of Local Deposition of Antigen on Salivary Immune Responses and Reaccumulation of Mutans Streptoccci," *M. Clin. Immunol.*, 10(5):273–281 (1990). Smith, D. J., et al., "Antigenicity and Immunogenicity of a Synthetic Peptide Derived from a Glucan–Binding Domain of Mutans Streptoccal Glucosyltransferase," *Infect. Immun.*, 61(7):2899–2905 (1993).

Smith, D. J., et al., "Immunogenicity and Protective Immunity Induced by Synthetic Peptides Associated with a Catalytic Subdomain of Mutans Group Streptococcal Glucosyltransferase," *Infect. Immunity*, 65(11):4424–4430 (1997).

Smith, D. J., et al., "Effects of Local Immunization of Hamsters with Glucosyltransferase Antigens From *Streptococcus sanguis* on Dental Caries Caused by *Streptococcus mutans*," *Archs. Oral Biol.*, 26:871–878 (1981).

(List continued on next page.)

Primary Examiner—Rodney P Swartz
(74) Attorney, Agent, or Firm—Ingrid A. Beattie; Janine M. Susan; Mintz, Levin, Cohn, Ferris, Glovsky and Popeo, P.C.

(57) ABSTRACT

Vaccine compositions and immunogenic compositions are described which are glucosyltransferase subunit vaccines for dental caries and which contain at least one peptide which corresponds to a sequence of glucosyltransferase containing aspartate 413, an equivalent of aspartate 413, aspartate 451, an equivalent of aspartate 451, aspartate 562, and equivalent of aspartate 562, aspartate 567, an equivalent of aspartate 567, histidine 561, an equivalent of histidine 561, tryptophan 491, an equivalent of tryptophan 491, glutamate 489, an equivalent of glutamate 489, arginine 449, an equivalent of arginine 449, or combinations thereof. These subunit vaccines elicit antibodies which protect an immunized mammal from dental caries. Methods of provoking an immune response to intact glucosyltransferase are also described.

28 Claims, 2 Drawing Sheets

OTHER PUBLICATIONS

Taubman, M. A., et al., "Communication with Complementary Glucosyltransferase Peptides Results in Enhanced Immunogenicity and Protection against Dental Caries," *Infect, Immun.*, 68(5):2698–2703 (2000).

Smith, D. J. and M. A. Taubman, "Oral Immunization of Humans with *Streptococcus sobrinus* Glucosyltransferase," *Infect. Immunity*, 55(11):2562–2569 (1987).

Jespergaard, C., et al., "Functional and Immunogenic Characterization of Two Cloned Regions of *Streptococcus mutans* Glucosyltransferase I," *Infect. Immunity.*, 67(2):810–816 (1999).

Jespergaard, C., et al., "Protective Immunity Against *Streptococcus mutans* Infection in Mice After Intranasal Immunization with the Glucan–Binding Region of *S. mutans* Glucosyltransferase," *Infect. Immunity*, 67(12):6543–6549 (1999).

Smith, D. J., et al., "Facilitated Intranasal Induction of Mucosal and Systemic Immunity to Mutans Streptococcal Glucosyltransferase Peptide Vaccines," *Infect. Immun.*, 69(8):4767–4773 (2001).

Taubman, M. A., et al., "Diepitopic Construct of Functionally relevant complementary peptides enhances immunogenicity reactivity with glucosyltransferase and protection against Dental Caries," *Infect. Immun.*, 69:4210–4216 (2001).

Smith, D. J., et al., "Induction of Secretory Immunity with Bioadhesive Poly (D,L–lactide–co–glycolide) Microparticles Containing *Streptococcus sobrinus* Glucosyltransferase," *Oral Microbiology and Immunology*, 15:124–130 (2000).

Smith, D. J., et al., "Facilitated Intranasal Induction of Mucosal and Systemic Immunity to Mutans Streptococcal Glucosyltransferase Peptide Vaccines," *Infection and Immunity*, 69(8):4767–4773 (2001).

Chia, Jean–San, et al., "Inhibition of Glucosyltransferase Activities of *Streptococcus mutans* by a Monoclonal Antibody to a Subsequence Peptide", *Infection and Immunity*, 61(11):4689–4695 (1993).

Dertzbaugh, Mark T. and Macrina, Francis L., "Inhibition of *Streptococcus mutans* Glucosyltransferase Activity by Antiserum to a Subsequence Peptide", *Infection and Immunity*, 58(6):1509–1513 (1990).

Dertzbaugh, Mark T., et al., "Cholera Toxin B–Subunit Gene fusion: Structural and Functional Analysis of the Chimeric Protein", *Infection and Immunity*, 58(1):70–79 (1990).

Devulapalle, Kumari S., et al., "Knowledge–Based Model of a Glucosyltransferase from the Oral Bacterial Group of Mutans Streptococci", *Protein Science*, 6:2489–2493 (1997).

Ferretti, Joseph J., et al., "Nucleotide Sequence of a Glucosyltransferase Gene from *Streptococcus sobrinus* MFe328", *Journal of Bacteriology*, 169(9):4271–4278 (1987).

Ferretti, Joseph J., et al., "Sequence Analysis of the Glucosyltransferase A Gene (gtfA) from *Streptococcus mutans* Ingbritt", *Infection and Immunity*, 56(6):1585–1588 (1988).

Funane, Kazumi, et al., "An Active–Site Peptide Containing the Second Essential Carboxyl Group of Dextransucrase from *Leuconostoc mesenteroides* by Chemical Modifications", *Biochemistry*, 32:13696–13702 (1993).

Jenkins, John, et al., "β–Glucosidase, β–galactosidase, Family A Cellulases, Family F Xylanases and Two Barley glycanases Form a Superfamily of Enzymes with 8–fold β/α Architecture and with Two Conserved Glutamates Near the Carboxy–terminal Ends of β–strands Four and Seven", *FEBS Letters*, 362:281–285 (1995).

MacGregor, E. Ann, et al., "A Circularly Permuted α–amylase–type α/β–barrel Structure in Glucan–synthesizing Glucosyltransferases", *FEBS Letters*, 378:263–266 (1996).

Matsuura, Yoshiki, et al., "Structure and Possible Catalytic Residues of Taka–Amylase A", *J. Biochem.* 95:697–702 (1984).

Mooser, G., et al., "Sequence of a Catalytically Significant Active Site Peptide from Two *S. sorbinus* Glucosyltransferases", *J. Dental Res.*, 69:325 (1990) Abstract 1729.

Mooser, Gregory, et al., "Isolation and Sequence of an Active–site Peptide Containing a Catalytic Aspartic Acid from Two *Streptococcus sobrinus* α–Glucosyltransferases", *The Journal of Biological Chemistry*, 266(14):8916–8922 (1991).

Russell, R. R. B., et al., "Homology of Glucosyltransferase Gene and Protein Sequences from *Streptococcus sobrinus* and *Streptococcus mutans*", *J. Dental Res.* 67(3):543–547 (1988).

Shimamura, Atsunari, et al., "Identification of Amino Acid Residues in *Streptococcus mutans* Glucosyltransferases Influencing the Structure of the Glucan Product", *Journal of Bacteriology*, 176(16):4845–4850 (1994).

Smith, Daniel J., et al., "Peptides Associated with the $\beta_5$ Barrel Element of Glyucostyltransferase (GTF) Induce GTF–Reactive and –Inhibitory Antibody", *J. Dental Res.* 78:422 (1999).

Smith, D. J., et al., "Immunological Features of a Novel Histidine–Containing Peptide Associated with GTF Catalytic Activity", *J. Dent. Res.*, 77:734 (1998), Abstract 818.

Smith, Daniel J., et al., "Immunological Characteristics of a Snythetic Peptide Associated with a Catalytic Domain of Mutans Streptococcal Glucosyltransferase", *Infect. Immun.* 62(12):5470–5476 (1994).

Søgaard, Morten, et al., "Site–Directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley α–Amylase 1", *The Journal of Biological Chemistry*, 268(30):22480–22484 (1993).

Taubman, Martin A., et al., "Immunization of Rats with Synthetic Peptide Constructs from the Glucan–Binding or Catalytic Region of Mutans Streptococcal Glucosyltransferase Protects Against Dental Caries", *Infection and Immunity*, 63(8):3088–3093 (1995).

Taubman, M. A., et al., "Diepitopic Construct of Functionally Relevant Peptides Enhances Immunogenicity and Reactivity with Glucosyltransferase", *J. Dent. Res.*, 76:347 (1997), Abstract 2666.

Taubman, M. A., et al., "Immune Properties of Glucosyltransferases from *S. sorbrinus*", *J. Oral Pathol.* 17:466–470 (1988).

Tsumori, H., et al., "Identification of Essential Amino Acids in the *Streptococcus mutans* Glucosyltransferases", *Journal of Bacteriology,* 179(11):3391–3396 (1997).

Ueda, Shunsaku, et al., "Sequence Analysis of the gtfC Gene from *Streptococcus mutans* GS–5", *Gene* 69:101–109 (1988).

Smith, Daniel J., et al., "Antibody to Glucosyltransferase Induced by Synthetic Peptides Associated with Catalytic Regions of α–Amylases", Infection and Immunity, 67(5):2638–2642 (1999).

U.S. application No. 08/967,573 filed Nov. 10, 1997, titled "Synthetic Peptide Vaccines for Dental Carries" by Daniel J. Smith and Martin A. Taubman.

* cited by examiner

```
                        SEQUENCE LISTING

<160> NUMBER OF SEQ ID NOS: 19

<210> SEQ ID NO 1
<211> LENGTH: 21
<212> TYPE: PRT
<213> ORGANISM: Artificial Sequence
<220> FEATURE:
<223> OTHER INFORMATION: EAW peptide

<400> SEQUENCE: 1

Ala Asn Asp His Leu Ser Ile Leu Glu Ala Trp Ser Asp Asn Asp Thr
1               5                   10                  15

Pro Tyr Leu His Asp
            20

<210> SEQ ID NO 2
<211> LENGTH: 20
<212> TYPE: PRT
<213> ORGANISM: Artificial Sequence
<220> FEATURE:
<223> OTHER INFORMATION: HDS peptide

<400> SEQUENCE: 2

Val Pro Ser Tyr Ser Phe Ile Arg Thr Ala His Asp Ser Glu Val Gln
1               5                   10                  15

Asp Leu Ile Ala
            20

<210> SEQ ID NO 3
<211> LENGTH: 22
<212> TYPE: PRT
<213> ORGANISM: Artificial Sequence
<220> FEATURE:
<223> OTHER INFORMATION: GLB peptide

<400> SEQUENCE: 3

Thr Gly Ala Arg Thr Ile Asn Gly Gln Leu Leu Tyr Phe Arg Ala Asn
1               5                   10                  15

Gly Val Gln Val Lys Gly
            20

<210> SEQ ID NO 4
<211> LENGTH: 15
<212> TYPE: PRT
<213> ORGANISM: Artificial Sequence
<220> FEATURE:
<223> OTHER INFORMATION: MAC peptide

<400> SEQUENCE: 4

Pro Gln Trp Asn Gly Glu Ser Glu Lys Pro Tyr Asp Asp His Leu
1               5                   10                  15

<210> SEQ ID NO 5
<211> LENGTH: 15
<212> TYPE: PRT
<213> ORGANISM: S. mutans
```

```
<400> SEQUENCE: 5

Ser Ala Trp Asn Ser Asp Ser Glu Arg Pro Phe Asp Asp His Leu
1               5                   10                  15

<210> SEQ ID NO 6
<211> LENGTH: 15
<212> TYPE: PRT
<213> ORGANISM: S. mutans

<400> SEQUENCE: 6

Ser Ala Trp Asn Ser Asp Ser Glu Lys Pro Phe Asp Asp His Leu
1               5                   10                  15

<210> SEQ ID NO 7
<211> LENGTH: 15
<212> TYPE: PRT
<213> ORGANISM: S. mutans

<400> SEQUENCE: 7

Pro Asn Trp Asn Ser Gln Thr Glu Ser Asp Thr Ser Ala Gly Glu
1               5                   10                  15

<210> SEQ ID NO 8
<211> LENGTH: 15
<212> TYPE: PRT
<213> ORGANISM: S. downei

<400> SEQUENCE: 8

Pro Gln Trp Asn Gly Glu Ser Glu Lys Pro Tyr Asp Asp His Leu
1               5                   10                  15

<210> SEQ ID NO 9
<211> LENGTH: 15
<212> TYPE: PRT
<213> ORGANISM: S. sobrinus

<400> SEQUENCE: 9

Pro Gln Trp Asn Gly Glu Ser Glu Lys Pro Tyr Asp Asp His Leu
1               5                   10                  15

<210> SEQ ID NO 10
<211> LENGTH: 21
<212> TYPE: PRT
<213> ORGANISM: S. mutans

<400> SEQUENCE: 10

Ala Asn Asp His Leu Ser Ile Leu Glu Ala Trp Ser Asp Asn Asp Thr
1               5                   10                  15

Pro Tyr Leu His Asp
            20

<210> SEQ ID NO 11
<211> LENGTH: 21
<212> TYPE: PRT
<213> ORGANISM: S. mutans

<400> SEQUENCE: 11

Ala Ile Asn His Leu Ser Ile Leu Glu Ala Trp Ser Asp Asn Asp Pro
1               5                   10                  15

Gln Tyr Asn Lys Asp
            20
```

```
<210> SEQ ID NO 12
<211> LENGTH: 21
<212> TYPE: PRT
<213> ORGANISM: S. downei

<400> SEQUENCE: 12

Ala Asn Asn His Val Ser Ile Val Glu Ala Trp Ser Asp Asn Asp Thr
 1               5                  10                  15

Pro Tyr Leu His Asp
            20

<210> SEQ ID NO 13
<211> LENGTH: 21
<212> TYPE: PRT
<213> ORGANISM: S. downei

<400> SEQUENCE: 13

Ala Ile Asp His Leu Ser Ile Leu Glu Ala Trp Ser Gly Asn Asp Asn
 1               5                  10                  15

Asp Tyr Val Lys Gln
            20

<210> SEQ ID NO 14
<211> LENGTH: 21
<212> TYPE: PRT
<213> ORGANISM: S. sobrinus

<400> SEQUENCE: 14

Ala Asn Asn His Val Ser Ile Val Glu Ala Trp Ser Asp Asn Asp Thr
 1               5                  10                  15

Pro Tyr Leu His Asp
            20

<210> SEQ ID NO 15
<211> LENGTH: 22
<212> TYPE: PRT
<213> ORGANISM: S. mutans

<400> SEQUENCE: 15

Val Pro Ser Tyr Ser Phe Ile Arg Ala His Asp Ser Glu Val Gln Asp
 1               5                  10                  15

Leu Ile Arg Asn Ile Ile
            20

<210> SEQ ID NO 16
<211> LENGTH: 22
<212> TYPE: PRT
<213> ORGANISM: S. mutans

<400> SEQUENCE: 16

Met Ala Asn Tyr Ile Phe Ile Arg Ala His Asp Ser Glu Val Gln Thr
 1               5                  10                  15

Val Ile Ala Lys Ile Ile
            20

<210> SEQ ID NO 17
<211> LENGTH: 22
<212> TYPE: PRT
<213> ORGANISM: S. downei

<400> SEQUENCE: 17

Val Pro Ser Tyr Ser Phe Ala Arg Ala His Asp Ser Glu Val Gln Asp
 1               5                  10                  15
```

```
Leu Ile Arg Asp Ile Ile
            20

<210> SEQ ID NO 18
<211> LENGTH: 22
<212> TYPE: PRT
<213> ORGANISM: S. downei

<400> SEQUENCE: 18

Val Pro Asn Tyr Val Phe Ile Arg Ala His Asp Ser Glu Val Gln Thr
1               5                   10                  15

Arg Ile Ala Lys Ile Ile
            20

<210> SEQ ID NO 19
<211> LENGTH: 22
<212> TYPE: PRT
<213> ORGANISM: S. sobrinus

<400> SEQUENCE: 19

Val Pro Ser Tyr Ser Phe Ala Arg Ala His Asp Ser Glu Val Gln Asp
1               5                   10                  15

Ile Ile Arg Asp Ile Ile
            20
```

SYNTHETIC PEPTIDE VACCINES FOR DENTAL CARIES

RELATED APPLICATIONS

This application claims the benefit of U.S. provisional application Ser. No. 60/081,550 filed Apr. 13, 1998, and U.S. provisional application Ser. No. 60/115,142 filed Jan. 8, 1999, the entire teachings of which are incorporated herein by reference.

GOVERNMENT FUNDING

Work described herein was supported by grant numbers DE-04733 and DE-06153 awarded by the National Institutes of Health, National Institute of Dental Research. The U.S. Government has certain rights in the invention.

BACKGROUND OF THE INVENTION

Mutans streptococci have been convincingly implicated in the initiation of dental caries in humans. The ability of these organisms to accumulate and colonize on the tooth surface has been associated with the synthesis of glucans from sucrose. Glucans are synthesized by constitutively secreted glucosyltransferase (GTF) enzymes. These enzymes have been considered as potential components of a dental caries vaccine because of their role in the pathogenicity of Mutans streptococci. However, vaccines based on intact GTF have a variety of disadvantages, such as the presence of inappropriate epitopes and excess molecular material that does not possess appropriate immunogenic features.

It is quite likely that protection against dental caries will involve functional inhibition of the catalytic and/or the glucan-binding activities of GTF. Epitopes associated with these functions would theoretically be primary targets for immunological attack, provided that the relevant sequences are located in molecular areas that are accessible to antibody. Subunit vaccines provide a method to block functional domains without inducing immunity to irrelevant or unwanted epitopes. It has been reported that synthetic peptide vaccines associated with catalytic or glucan-binding domains of GTF can protect rats from experimental dental caries (Taubman et al., *Infect. Immun.* 63:3088–3093 (1995)). One of the peptides that was successfully used as a vaccine (Smith et al., *Infect. Immun.* 62:5470–5476 (1994)) demonstrated a sequence containing an aspartic acid (aspartate 451 in S. mutans GTF-B) to which the glucosyl moiety of sucrose was covalently bound (Mooser et al., *J. Biol. Chem.* 266:8916–8922 (1991)).

SUMMARY OF THE INVENTION

Mutans streptococcal GTFs may contain several sequentially separated residues that, partly because of secondary structure constraints (e.g., $(\beta,\alpha)_8$ barrel domain), have important functions in GTF catalytic mechanisms. Peptides containing catalytically implicated aspartates (Asp 413/415 or Asp 451, based on the sequence numbering of S. mutans GTF B) each induced antibody that inhibited GTF activity and protected rats from experimental dental caries. Recent site-directed mutagenesis and comparative sequence studies have implicated these sequentially separated residues in the catalytic activity of mutans streptococcal glucosyltransferases (GTF). The immunogenicity and induction of GTF-inhibitory activity of synthetic peptides which contained putative catalytic regions that were associated with the $\beta_5$ (EAW peptide) and $\beta_7$ (HDS peptide) strand elements of the suggested $(\beta,\alpha)_8$ catalytic barrel domain of GTF were examined. Both peptides induced serum IgG and salivary IgA anti-peptide activity twenty one days after the second injection. Serum IgG antibody induced by HDS and EAW peptide constructs also showed significant reaction with S. mutans GTF. Antisera to each peptide construct also inhibited the ability of S. mutans GTF to synthesize glucan. These observations support the existence of catalytic subdomains containing glutamate and tryptophan (EAW) or aspartate and histidine (HDS) residues which have been suggested to be involved with the catalytic activity of GTF. Furthermore, the epitope(s) defined in these sequences have significant immunogenicity and can induce immune responses which interfere with GTF-mediated glucan synthesis.

This invention pertains to subunit vaccine compositions which elicit immune system responses in mammals to glucosyltransferase (GTF), an enzyme that is implicated in the formation of dental caries, or to subunits thereof. Rather than using intact GTF as an immunizing agent, the vaccine composition or immunogenic composition is prepared from particular immunogenic portions (subunits) of GTF.

The invention relates to vaccine compositions and immunogenic compositions comprising at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. In particular embodiments, the amino acid sequence is selected from the group consisting of 481-ANDHLSILEAWSDNDTPYLHD (EAW peptide; SEQ ID NO: 1); and 552-VPSYSFIRAHDSEVQDLIA (HDS peptide; SEQ ID NO: 2). These peptides are believed to be from the catalytic domain of GTF and have been shown to induce high levels of antibody that crossreact with intact GTF.

In another embodiment, the invention relates to a peptide having the amino acid sequence 1300-TGARTINGQLLYFRANGVQVKG (GLB peptide; SEQ ID NO: 3); this sequence is believed to be from the glucan binding region of GTF.

In a particularly preferred embodiment, 2 or more of the peptides are present and arranged on a core matrix of 3 or more lysines.

The invention also relates to vaccine compositions and immunogenic compositions comprising at least two peptides covalently attached to a peptidyl core matrix, wherein each peptide consists essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. In a particular embodiment, the amino acid sequence is selected from the group consisting of the EAW peptide (ANDHLSILEAWSDNDTPYLHD; (SEQ ID NO: 1)) and the HDS peptide (VPSYSFIRADSEVQDLIA; (SEQ ID NO: 2)). In another embodiment, the peptide is the GLB peptide (TGARTINGQLLYFRANGVQVKG; (SEQ ID NO: 3)). In additional embodiments, the composition further comprises at least one additional immunologic component covalently attached to said peptidyl core matrix. For example, the additional immunologic component can be an immunogenic portion of a pathogen selected from the group consisting of diphtheria, pertussis, tetanus, measles and polio vaccines.

The invention also pertains to a method of provoking an immune response to glucosyltransferase in mammals comprising administering to a mammal at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, which is of sufficient length to raise an immune response in the mammal, thereby provoking said immune response. In a preferred embodiment, the immune response results in reduction of the colonization or accumulation of mutans streptococcal strains in the mammal to whom the peptide is administered.

The invention further pertains to a method of immunizing a mammal against dental caries comprising administering to the mammal at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in the mammal.

DETAILED DESCRIPTION OF THE INVENTION

Figure 1:
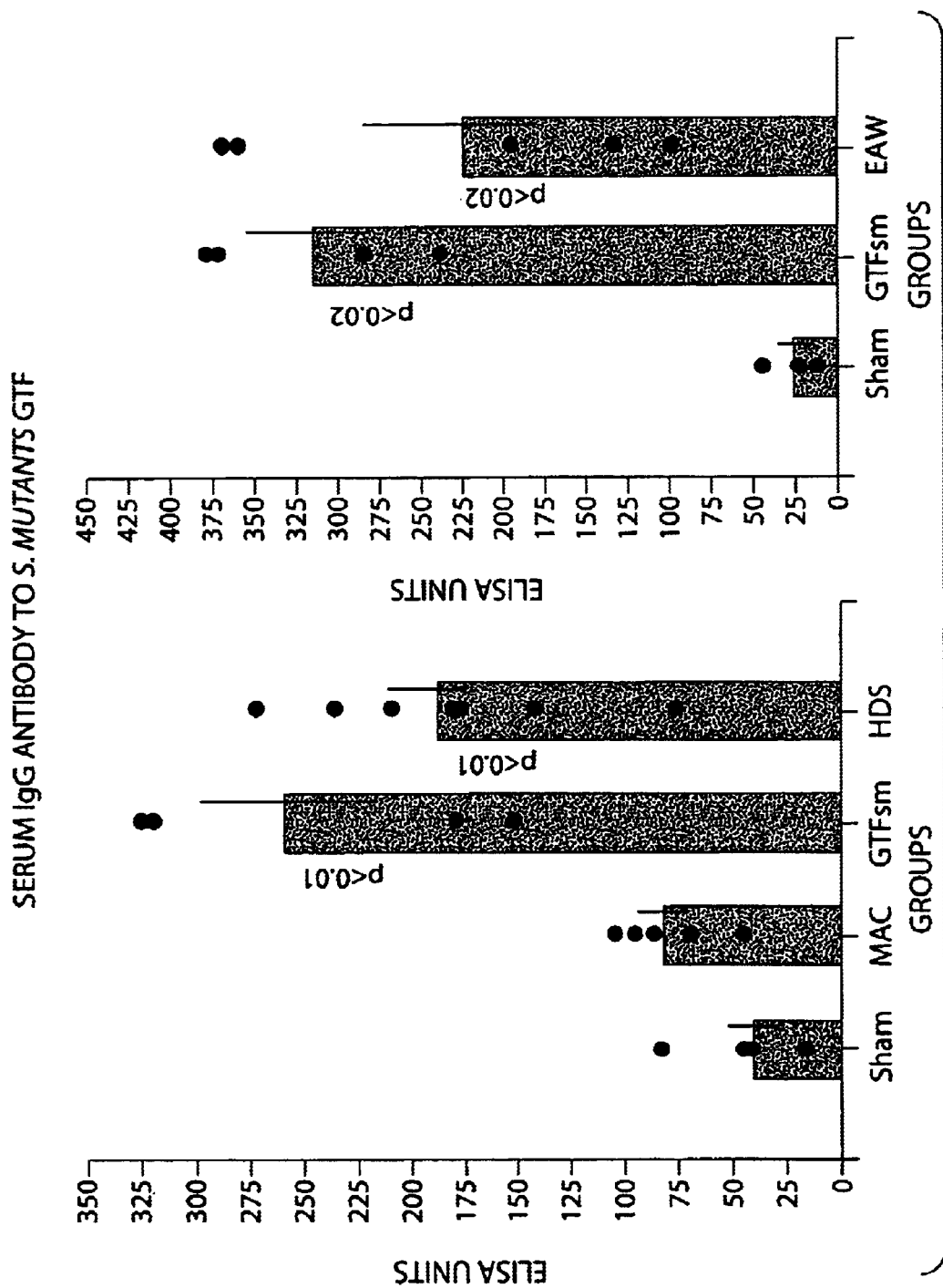
FIG. 1 is a graph showing the results when IgG antibody reactivities to S. mutans GTF were evaluated in ELISA in rat sera taken 42 days after initial injection (2 injections). The left and right panels represent different experiments utilizing identical immunization protocols. Bars indicate the mean absorbance for all rat sera of the indicated group (n=4–7), tested at 1:400 dilutions, at least in duplicate. Vertical bars indicate two standard errors. The levels of significance, compared with the sham group, using the Kruskal-Wallace ANOVA on ranks, are indicated alongside the bars.

The principal etiologic agents of dental caries are Mutans streptococci. These oral pathogens infect the oral cavity during early childhood and normally remain associated with the host's definition for life. Mutans streptococci must colonize and then accumulate on the tooth surface in sufficient numbers to achieve dissolution of the enamel. After the initial colonization by Mutans streptococci on the tooth surface, the Mutans streptococci produce glucosyltransferase (GTF), an enzyme which catalyzes the synthesis of glucans from sucrose. In addition, S. mutans express cell surface proteins which serve as glucan binding sites. Glucans mediate much of the subsequent accumulation of Mutans streptococci on the tooth surface. This results in an increase in the numbers of potentially cariogenic bacteria in plaque. The metabolism of various saccharides by the accumulated bacterial mass results in excretion of significant amounts of lactic acid as a metabolic product, which causes demineralization when present in sufficient amount in close proximity to the tooth surface. This eventually results in a carious lesion (a cavity).

Recently, primary and secondary structural comparisons of glucosyltransferases with the alpha amylase superfamily have provided insights into the structure-function relationships of the GTF catalytic domain. Much of the catalytic activity of alpha amylases is contained in a $(\beta,\alpha)_8$ barrel element (Matsuura, et al., *J. Biochem.* 95:697–702 (1984)). Aspartates or glutamates at the C terminus of β strands (Dertzbaugh, et al., *Infect. Immun.* 58:70–79 (1990); Devulapalle, et al., *Protein Science* 6:2489–2493 (1997); Funane, et al.,*Biochem.* 32:13696–13702 (1993)) have been specifically implicated in amylolytic activity and are invariant in these enzymes (Jenkins, et al., *FEBS Lett.* 362:281–285 (1995)). The overall homology between alpha amylases and GTF is low, except for a 50–60 amino acid sequence stretch near the middle of the GTF molecule (Ferretti, et al., *J. Bacteriol.* 169:4271–4278 (1987)) for which no catalytically involved residues have been identified. However, sequence alignment techniques (Devulapalle, et al., *Protein Science* 6:2489–2493 (1997); MacGregor, et al., *FEBS Let.* 378:263–266 (1996)) have shown significant homologies between GTFs and alpha amylase with respect to several invariant residues important to the catalytic activity of the alpha amylase family, and have suggested that the $(\beta,\alpha)_8$ barrel element may also be a feature of the GTF catalytic domain. Strengthening this conclusion are site-directed mutagenesis studies (Devulapalle, et al., *Protein Science* 6:2489–2493 (1997); Tsumori, et al., *J. Bacteriol*, 179:3391–3396 (1997)) which showed that modification of aspartates or glutamates in GTF, which aligned with the catalytically important residues in the β4, β5, and β7 strands of alpha amylases, drastically reduced GTF catalytic activity.

Since residues in or near the putative β5 and β7 strands of GTF thus appear to be functionally important, it was of interest to determine whether significant antigenic epitopes exist within these sites of GTF catalytic activity and whether antibody to these putative epitopes could inhibit enzyme activity. Under the hypothesis that sequential epitopes within these regions could be mimicked by synthetic peptides, two synthetic peptide constructs were prepared whose sequences contained the β5 and β7 strands, as well as adjacent residues that were implicated in catalytic activity by modeling and site-directed mutagenesis techniques (MacGregor et al., *FEBS Let.* 378:263–266 (1996); Tsumori et al., *J. Bacteriol*, 179:3391–3396 (1997)). These peptide constructs were then assessed for their ability to induce serum IgG and salivary IgA antibody to peptide and to S. mutans GTF, as well as for their ability to inhibit the catalytic activity of mutans streptococcal GTF.

The compositions of the present invention, e.g., vaccine compositions and immunogenic compositions, comprise at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. The desired effect of these compositions is interruption of the cariogenic process, resulting in reduction, i.e., lessening or prevention, of dental caries.

The primary sequences of several mutans streptococcal GTFs have been deduced from DNA studies (Ferretti et al., *Infect. Imm.* 56:1585–1588 (1988); Russell et al., *J. Dental Res.* 67:543–547 (1988); Ueda et al., *Gene* 69 101–109 (1988)). Although GTFs are large molecules, they function through a few discrete sites, which include the catalytic and glucan-binding sites. Primary sequences have been identified which provisionally include these sites (Mooser et al., *J. Dental Res.* 69:325 (1990); Russell et al., *J. Dental Res.* 67:543–547 (1988)).

As used herein, a vaccine composition is a composition which elicits an immune response in a mammal to which it is administered and which protects the immunized mammal against subsequent challenge by the immunizing agent or an immunologically cross-reactive agent. Protection can be complete or partial (i.e., a reduction in symptoms or infection as compared with an unvaccinated mammal). An immunologically cross-reactive agent can be, for example, the whole protein (e.g., glucosyltransferase) from which a sub-unit peptide used as the immunogen is derived. Alternatively, an immunologically cross-reactive agent can be a different protein which is recognized in whole or in part by the antibodies elicited by the immunizing agent.

As used herein, an immunogenic composition is intended to encompass a composition which elicits an immune response in a mammal to which it is administered and which may or may not protect the immunized mammal against subsequent challenge with the immunizing agent.

Peptides which are particularly useful in the present invention are peptides which consist essentially of an amino acid sequence of GTF comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof. For example, the amino acid sequence can be the amino acid sequence of the EAW peptide (ANDHLSILEAWSDNDTPYLHD; (SEQ ID NO: 1)) or the HDS peptide (VPSYSFIRAfDSEVQDLIA; (SEQ ID NO: 2)). The invention also relates to the GLB peptide (TGARTINGQLLYFRANGVQVKG; (SEQ ID NO: 3)). Appropriate amino acid sequences will contain one or more of aspartate 413, aspartate 451, aspartate 562, aspartate 567, histidine 561, tryptophan 491, glutamate 489, arginine 449, or equivalents of these amino acids. Aspartate 413, aspartate 451, aspartate 562, and aspartate 567 refer to the aspartate residues at amino acid positions 413, 451, 562 and 467, respectively, of S. mutans GTF-B. As used herein, equivalents of these aspartate residues are intended to include catalytic aspartate residues present at equivalent sites (positions) in other mutans streptococcal GTFs (see, for example, Table 1). That is, the amino acid position numbers of the aspartate residues can be different from 413, 451, 562, and 567 in other mutans streptococcal GTFs. These equivalent aspartate residues can be identified, for example, by aligning the amino acid sequences of other streptococcal GTFs based on homology to S. mutans GTF-B using methods known in the art. In addition, the characterization of the catalytic properties of an aspartate which is equivalent to aspartate 413, 451, 562, or 567 can be determined by methods described herein or methods known in the art (see, for example, Funane et al., *Biochem.* 32:13696–13702 (1993)).

Similarly, histidine 561, tryptophan 491, glutamate 489 and arginine 449 refer to the histidine, tryptophan, glutamate and arginine residues, respectively, at amino acid positions 561, 491, 489 and 449, respectively, of S. mutans GTF-B. As used herein, equivalents of these histidine, tryptophan, glutamate and arginine residues are intended to include histidine, tryptophan, glutamate and arginine residues, respectively, present at equivalent sites (positions) in other mutans streptococcal GTFs (see, for example, Table 1). That is, the amino acid position numbers of these residues can be different in other mutans streptococcal GTFs. These equivalent residues can be identified, for example, by aligning the amino acid sequences of other streptococcal GTFs based on homology to S. mutans GTF-B. In addition, the characterization of the properties of amino acid residues which are equivalent to, e.g., histidine 561 can be determined by methods described herein or methods known in the art (see, for example, Funane et al., *Biochem.* 32:13696–13702 (1993)).

Useful peptides will be of sufficient length to raise an immune response in a mammal to whom it is administered but will be less than the complete amino acid sequence of the intact GTF enzyme. Typically, the peptide will be at least 5–7 amino acids in length. Preferably the peptide will be at least 12 amino acids in length; more preferably the peptide will be at least 19, 20 or 21 amino acids in length.

The immune response which is raised can comprise a B cell response, a T cell response or both a B cell and T cell response. The B cell response is associated with the appearance of mucosal antibody, which is predominately IgA, and systemic antibody, which is predominantly IgG. The antibodies elicited by immunization will preferably recognize both the immunizing agent and an immunologically cross-reactive agent. In a preferred embodiment the antibody response will be sufficient to protect the immunized mammal against subsequent challenge or infection with the immunizing agent or an immunologically cross-reactive agent.

Although the vaccine composition of the present invention can contain one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered, preferred embodiments of the vaccine composition of the present invention contain two or more of such peptides.

Those skilled in the art will be able to determine other immunologic domains of GTF, as well as additional immunologic components of non-GTF origin which enhance adjuvanticity or produce an immunogenic response against other infectious agents, suitable for use in the vaccine composition. For example, the peptides disclosed herein can be valuably combined in a vaccine or immunogenic composition with one or more CAT, GLU, GGY, AND or SAND peptides or surface binding domain peptides such as those disclosed in U.S. Pat. No. 5,686,075 and in U.S. patent application Ser. No. 08/967,573 (Smith and Taubman), the entire teachings of which are incorporated herein by reference. In particular embodiments, the vaccine or immunogenic composition of the present invention can comprise an additional immunologic component which is an immunogenic portion of a pathogen such as, but not limited to, diphtheria, pertussis, tetanus, measles and polio virus, resulting in a multivalent vaccine producing protection against more than one infectious disease or agent. Ultimately, a multivalent vaccine can be produced which incorporates relevant protective epitopes and appropriate adjuvant sequences targeting early childhood infections.

The peptides present in the vaccine composition of the present invention may be designed in a number of ways to enhance immunogenicity. In one embodiment in which the vaccine composition contains one or more peptides, the peptide is conjugated to a known protein, (such as tetanus toxoid) or a carrier (such as a synthetic polymer carrier) to give a macromolecular structure to the vaccine which thereby enhances immunogenicity. In a preferred embodiment in which the vaccine composition contains at least two peptides, the peptides are synthesized and covalently attached to a peptidyl core matrix to yield a macromolecule with a high density of peptides in a single structure. Each peptide in such a structure consists essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. The peptidyl core matrix can consist of amino acids such as lysine, arginine and histidine. In particular, at least 2 peptides are synthesized on a core matrix of at least one lysine to yield a macromolecular vaccine composition. Particularly, at least 2 peptides are synthesized on a core matrix of 3 lysines. In a preferred embodiment, a vaccine composition is designed in which four peptides of the present invention are synthesized and covalently attached to a core matrix of 3 lysines yielding a radially branched peptide with four dendritic arms. In this embodiment, the four peptides present can be the same or different. Those skilled in the art will be able to determine other variations of synthesizing and covalently attaching vaccine compositions of the present invention to a peptidyl core matrix by employing routine experimentation.

The present invention also pertains to pharmaceutical compositions comprising at least one peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. For instance, the peptide of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous peptides at the site of treatment include, but are not limited to, intradermal, intramuscular, intraperitoneal, intravenous, subcutaneous, oral, sublingual, intraocular and intranasal. Other suitable methods of introduction can also include rechargeable or biodegradable devices and slow release polymeric devices. The pharmaceutical compositions of this invention can also be administered as part of a combinatorial therapy with other agents.

The present invention also relates to antibodies which bind a polypeptide of the present invention. For instance, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); WO 97/08320 (Morphosys) and U.S. Pat. No. 5,225,539 (Winters)) which bind to the described polypeptides are within the scope of the invention. A mammal, such as a mouse, rat, hamster or rabbit, can be immunized with an immunogenic form of the polypeptide (e.g., a peptide comprising an antigenic fragment which is capable of eliciting an antibody response). Techniques for conferring enhanced immunogenicity on a protein or peptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, a polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). The term "antibody" as used herein is intended to include fragments thereof, such as Fab and $F(ab)_2$. Antibodies described herein can be used to inhibit the activity of GTF, particularly in vitro and in cell extracts, using methods known in the art. Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the polypeptide or GTF protein.

The present invention further relates to a method of provoking an immune response to glucosyltransferase in a mammal by administering a peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in a mammal to whom it is administered. Preferably, the immune response results in interference with the enzymatic activity of glucosyltransferase in mammals after administration of the vaccine composition. The immune response elicited by the compositions and methods of the invention can be humoral or systemic; for example, the immune response can be a mucosal response. The immune response elicited by the method of the present invention results in reduction of the colonization or accumulation of mutans streptococcal strains in the mammal to whom the vaccine or immunogenic composition is administered.

The invention also relates to a method of immunizing a mammal against dental caries comprising administering a peptide consisting essentially of an amino acid sequence of glucosyltransferase comprising an amino acid selected from the group consisting of aspartate 413, aspartate 451, aspartate 562, aspartate 567, histidine 561, tryptophan 491, glutamate 489, arginine 449, an equivalent of aspartate 413, an equivalent of aspartate 451, an equivalent of aspartate 562, an equivalent of aspartate 567, an equivalent of histidine 561, an equivalent of tryptophan 491, an equivalent of glutamate 489, an equivalent of arginine 449, and combinations thereof, and which is of sufficient length to raise an immune response in the mammal, to the mammal.

The compositions of the present invention can be administered to any mammal in which the prevention and/or reduction of dental caries is desired. Suitable mammals include primates, humans, cats, dogs, mice, rats and other mammals in whom it is desirable to inhibit dental caries. The present invention provides a vaccine that is useful for preventing, halting or reducing the progression of dental caries in a mammal to whom the vaccine is administered.

In the method of the present invention of provoking an immune response to glucosyltransferase, mammals in which an immune response to glucosyltransferase is desired are given the vaccine or immunogenic compositions described herein. The vaccine composition can be included in a formulation which is administered to an individual being treated; such a formulation can also include a physiologically compatible carrier (e.g., a physiological buffer), stabilizers, flavorants, adjuvants and other components. The vaccine can be administered by a variety of routes (e.g., parenterally, intranasally, intraocularly, intravenously, orally) and the components of the formulation will be selected accordingly. The amount to be administered and the frequency of administration can be determined empirically and will take into consideration the age and size of the mammal being treated and the stage of the dental caries disease (e.g., prior to colonization of Mutans streptococci, soon after colonization of Mutans streptococci or in later stages of colonization).

Studies (Taubman et al., *J. Dent. Res.* 76:347 (1997)) indicate that multiepitopic peptide constructs induce enhanced immune responses. This strategy also could be used to increase the immune potential of the EAW/HDS/GLB peptide sequences described herein. Moreover, the combination of sequences from several strains into a synthetic or recombinant multi-epitopic construct could increase the protective potential of subunit vaccines for dental caries.

Figure 2:
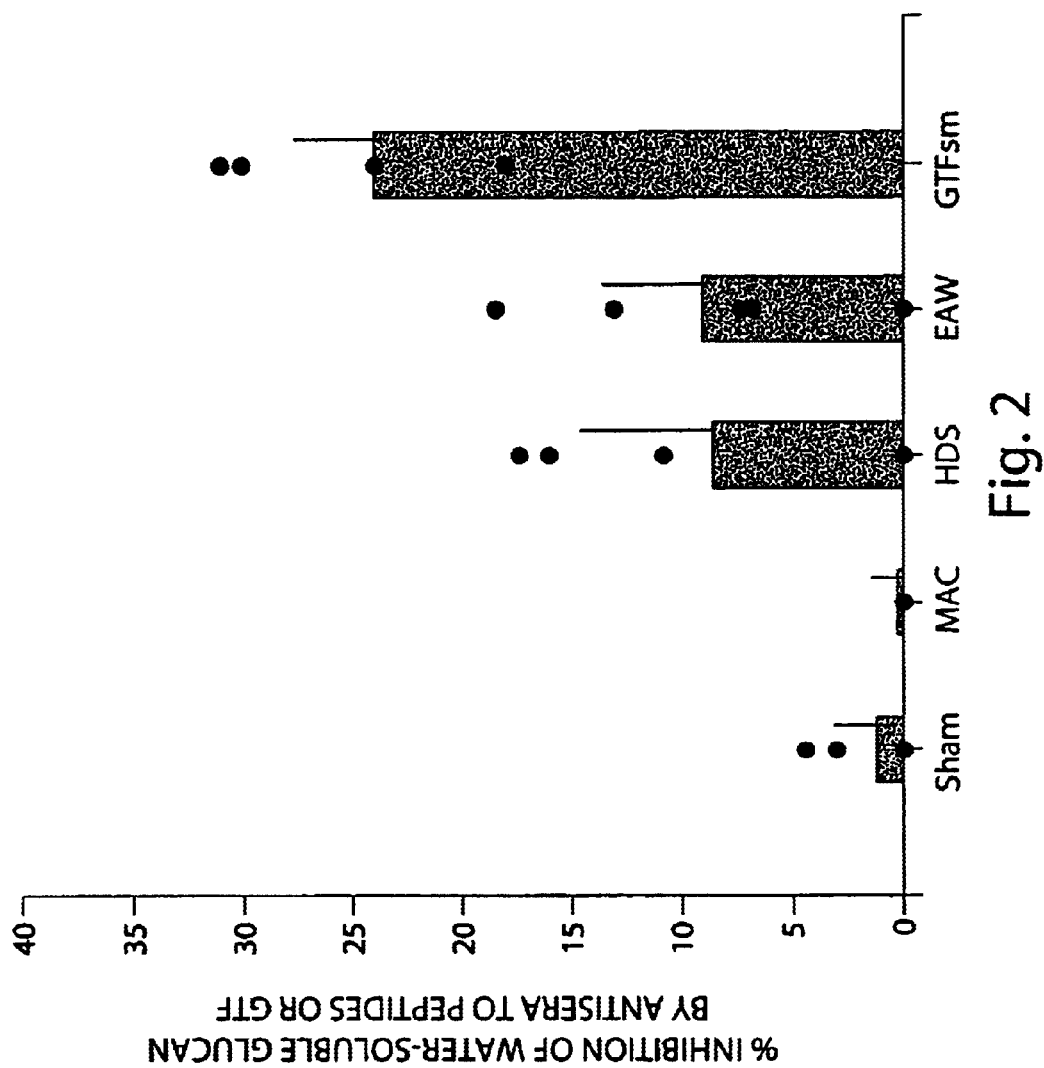
FIG. 2 is a graph showing the percent inhibition of the S. mutans GTF-mediated incorporation of $^{14}C$ glucose from labeled sucrose into water-soluble glucan by sera from peptide or GTF-injected rats. Bars indicate the mean inhibition for rat sera (n=4–6) of the indicated peptide-injected groups, tested at 1:10 dilutions, or the S. mutans GTF-injected group, tested at 1:50 dilutions. The vertical bar indicates one standard deviation. Closed circles indicate the inhibition levels of individual rat sera. Data are expressed as the percent $^{14}C$ glucose incorporation of individual sera, compared with the mean $^{14}C$ glucose incorporation by four sera from sham-injected rats tested under the same protocol (mean incorporation=830 cpm).

Many lines of evidence suggest that mutans glucosyltransferases require the interaction of several sequentially separated amino acid residues for their catalytic activity. Sequence alignments of GTFs with alpha-amylases have suggested that a similar $(\beta,\alpha)_8$ barrel structure is present in the catalytic domain of both protein families (Devulapalle, et al., *Protein Science* 6:2489–2493 (1997)., MacGregor, et al., *FEBS Let.* 378:263–266 (1996)). Supporting this suggested structure is the observation that GTF activity can be significantly inhibited by site-directed mutagenesis of residues that correspond to invariant amino acids which are catalytically important in the $(\beta,\alpha)_8$ barrel domain of alpha amylases (Devulapalle, et al., *Protein Science* 6:2489–2493 (1997); Tsumori, H et al., *J. Bacteriol.* 179:3391–3396 (1997)). The immunological findings of the present study also support the catalytic importance of residues in equivalent GTF regions. In these studies, HDS and EAW (Table 1), two peptide constructs whose sequences are adjacent to the β5 and β7 strand elements of mutans streptococcal GTFs, induced high levels of serum IgG and salivary IgA antibody, not only to themselves (Tables 2 and 3), but also to S. mutans GTF (FIG. 1). Furthermore, these peptides also had the ability to induce antibody which could inhibit the water-soluble glucan synthetic activity of S. mutans GTF (FIG. 2).

Alpha amylases contain three catalytic sites which are located in or adjacent to the β4, β5 and β7 strands. Several catalytically involved amino acid residues have been implicated within analogous regions of GTF. One of these, an aspartate (Asp 451 in S. mutans GTF-B) corresponding to an invariant catalytic aspartate in the alpha amylase family (Asp 206 of taka-amylase A), has been shown by Mooser and coworkers (Mooser, et al.,*J. Bio. Chem.* 266:8916–8922 (1991)) to be involved in glucosyl-intermediate formation by GTF. It has been reported that the synthetic peptide construct, CAT, whose sequence contains the β4 strand and includes residues corresponding to the invariant Arg-449 and the above-mentioned Asp-451, can induce antibody that binds to intact GTF, significantly inhibits GTF activity, and can induce protective immunity for experimental dental caries (Smith, et al., *Infect. Immunity* 62:5470–5476 (1994), Taubman, et al., *Infect. Immun.* 63:3088–3093 (1995)). Recently, Devulapulle and Mooser (Devulapalle, et al., *Protein Science* 6:2489–2493 (1997)) mutated the comparable aspartate in *Streptococcus downei* GTF which resulted in an almost complete loss of catalytic activity.

Within the β5-associated strand of alpha amylases is a glutamate residue (position 230 in taka-amylase A) which is considered to serve catalytically as a proton donor (Matsuura, et al., *J. Biochem.* 95:697–702 (1984)). Site-directed mutagenesis of the analogous residue in *S. downei* GTF (Glu-489 in S. mutans GTF-B) to glutamine resulted in a catalytically inactive enzyme (Devulapalle, et al., *Protein Science* 6:2489–2493 (1997)). Mutagenesis of Trp-491 in S. mutans GTF-B, highly conserved in all mutans streptococcal GTFs (Table 1), also eliminated detectable enzyme activity (Tsumori, et al., *J. Bacteriol.* 179:3391–3396 (1997)). The EAW peptide sequence overlapped both of these important residues as well as the complete β5 strand sequence. Antibody induced by the EAW peptide construct could bind to and inhibit S. mutans GTF.

The HDS peptide construct contains several residues which have been implicated in GTF function. His-561 and Asp-562 in S. mutans GTF-B are invariant in mutans streptococcal GTFs. The analogous histidine in alpha amylases helps to stabilize transition states (Sogaard, et al., *J. Biol. Chem.* 268:22480–22484 (1993)), while the aspartate stabilizes the reaction intermediate carbonium cation (Matsuura, et al., *J. Biochem.* 95:697–702 (1984)). Site directed mutagenesis of the equivalent histidine and aspartic acid residues in mutans streptococcal GTFs catalytically inactivated the enzyme (Devulapalle, et al., *Protein Science* 6:2489–2493 (1997); Tsumori, et al., *J. Bacteriol.* 179:3391–3396 (1997)). Also contained within the HDS peptide sequence is an aspartate, equivalent to Asp-567 in GTF-B, which has been shown to influence the solubility of the glucan synthesized by GTF (Shimamura, et al., *J. Bact.* 176:4845–4850 (1994)). Aspartic acid is invariant at this position in all mutans streptococcal GTFs, although it is not conserved in alpha amylases, presumably because its function is irrelevant to amylolytic activity. Thus, antibody directed to the HDS peptide construct could be expected to influence several aspects of GTF activity. In the present study, most rats responded to HDS-peptide construct immunization with levels of antibody to GTF that were within the range of sera from rats injected with intact S. mutans GTF. Many of these sera also inhibited the water-soluble glucan synthetic activity of S. mutans GTF which is consistent with the presence of putative functional residues within this sequence.

Peptide-injected rat sera did not detectably inhibit water-insoluble glucan synthesis under the conditions of the assay. This lack of water-insoluble glucan inhibition may be related to the expected lower affinity and avidity of the anti-peptide antibody or be a consequence of assay conditions, such as the mixture of S. mutans GTF isotypes used for synthesis or the lack of primer dextran. Interestingly, antisera to intact S. mutans GTF also were less effective as inhibitors of water-insoluble, compared with water-soluble, glucan synthesis.

The MAC peptide construct was selected for control purposes, because its sequence (amino acids 342–356) lay outside the GTF $(\beta,\alpha)_8$ barrel domain predicted by MacGregor and coworkers (MacGregor et al., *FEBS Let.* 378:263–266 (1996)) or within a non-catalytically implicated approximately 200 residue loop within the $(\beta,\alpha)_8$ barrel domain of GTF predicted by Devulapalle and Mooser (Devulapalle et al., *Protein Science* 6:2489–2493 (1997)). Also this sequence bore no homology with sequences associated with catalytic function by biochemical (Funane et al., *Biochem.* 32:13696–13702 (1993); Mooser et al., *J. Biol. Chem.* 266:891&8922 (1991)) or molecular genetic techniques (Chia et al., *Immun.* 61:4689–4695 (1993, Devulapalle et al., *Protein Science* 6:2489–2493 (1997); Tsumori et al., *J. Bacteriol.* 179:3391–3396 (1997)). Neither serum IgG nor salivary IgA antibody to the HDS peptide construct showed any reactivity with the MAC peptide (Table 2). The MAC peptide construct was less immunogenic and induced less GTF-inhibitory antibody than did the HDS or EAW constructs, further supporting the catalytic significance of the residues within the latter two peptide sequences. Interestingly, a peptide sequence corresponding to MAC was immunogenic when fed (Dertzbaugh et al., *Infect. Immun.* 58:70–79 (1990)) or injected (Dertzbaugh and Macrina, *Immun.* 58:1509–1513 (1990)) as a protein chimera, fused to the sequence of the B subunit of cholera toxin (CTB). This difference in reactivity between the chimeric protein (Dertzbaugh and Macrina, *Immun.* 58:1509–1513 (1990)) and that of the MAC peptide construct could be because the former had highest homology with S. mutans GTF-B and GTF-C, while the MAC peptide in the present study was identical to the respective sequences in *S. sobrinus* and *S. downei* GTF-I (Table 1). In addition, the fusion with CTB undoubtedly influenced the immunogenicity of the protein chimera.

Thus, these data indicate that sequences containing functionally important residues associated with the β5 and β7 barrel elements are immunogenic and can induce systemic and mucosal antibody responses that can lead to loss of enzyme function. It has been shown that antibody levels induced by other catalytically associated peptides can be increased by combination with functionally associated GTF peptides that also contain a strong T cell epitope (Taubman et al., abstr. 2666, p. 347, In *J. Dent. Res.* 76 (1997)). Combination of HDS and or EAW with such peptides may also enhance immune responses to these important epitopes. Since both EAW and HDS peptide constructs also gave rise to significant levels of salivary IgA antibody in many animals, di- or multi-epitopic constructs could be expected to also increase mucosal immunity, thus potentiating their application as subunit vaccines for dental caries.

The invention will now be further illustrated by the following non-limiting examples. The teachings of all references cited herein are incorporated herein by reference in their entirety.

EXAMPLES

Materials and Methods

Peptide Constructs:

Three peptides were synthesized. Two of the sequences selected for synthesis (EAW and HDS) were based on putative catalytic regions within the predicted $(\beta,\alpha)_8$ barrel structure of GTF (Devulapalle et al., *Protein Science* 6:2489–2493 (1997); MacGregor et al., *FEBS Let.* 378:263–266 (1996)). EAW is a 21-mer peptide construct whose sequence contains the β5 strand sequence, as well as catalytically implicated Glu-489 and Trp491 (Table 1). HDS is a 19-mer peptide whose sequence contains the β7 strand sequence, as well as catalytically implicated His-561 and Asp-562 (Table 1). Both EAW and HDS sequences are highly conserved among all mutans streptococcal GTSs, and were identical to the respective S. mutans GTF-B sequence (Table 1). A third peptide (MAC) was synthesized to serve as a control for sequence outside the $(\beta,\alpha)_8$ barrel domain predicted by MacGregor and coworkers MacGregor et al., *FEBS Let.* 378:263–266 (1996)) and had 100% homology with the respective sequence of GTF-I of *S. sobrinus* and *S. downei*. Peptides were synthesized (Applied Diagnostics, Foster City, Calif.) using the stepwise solid phase method of Merrifield (Merrifield, *J. Amer. Chem. Soc.* 85:2149–2154 (1963)) on a core matrix of lysines to yield macromolecules with four identical peptides per molecule, after the method of Tam (Tam, *Proc. Natl. Acad. Sci. USA* 85:5409–5413 (1988)). Purity (>90%) was assessed using HPLC, amino acid analysis, and molecular weight determination by mass spectrometry.

Glucosyltransferases:

GTFs from S. mutans SJ and *S. sobrinus* 6715 were obtained as previously described (Smith, et al., *Infect. Immunity* 62:5470–5476 (1994); Taubman, et al., *J. Oral Pathol.* 17:466–470 (1988)). After bacterial growth in glucose-containing defined medium, enzymes were isolated from culture medium by affinity chromatography on Sephadex G-100 (Pharmacia Fine Chemicals, Piscataway, N.J.) with 3 M guandinine $HC_1$ as the eluting solvent. These GTF-rich pools were then subjected to FPLC liquid chromatography on Superose 6 (Pharmacia) with 6 M guanidine $HC_1$ for elution. The gel filtration step removes non-GTF and other glucan-binding proteins from GTF preparations, as evidenced by the fact that the protein bands observed after SDS-polyacrylamide gel electrophoresis were all associated with enzymatic activity after incubation of duplicate gels in sucrose. This S. mutans GTF preparation (GTFsm) synthesized both water insoluble and water soluble glucan in both tube and filter assays (Taubman, et al., *J. Oral Pathol.* 17:466–470 (1988)) and was used for injection, inhibition assays and ELISA measurements of antibody activity.

Immunogenicity of Peptides:

Sprague Dawley CD strain 42 day-old male rats (Charles River Laboratories, Wilmington, Mass.) were used for injection. Two experiments were performed. In the first experiment groups of 4–7 rats were injected subcutaneously in the vicinity of the salivary glands with 50 $\mu$g each of either HDS or MAC peptide constructs, or 10 $\mu$g of S. mutans GTF, or sham-immunized with buffer alone. In the second experiment groups of 4–6 rats were injected with 50 $\mu$g of the EAW peptide construct, 10 $\mu$g of S. mutans GTF, or sham-immunized. The remainder of the experimental protocol was identical. The initial injection included complete Freund adjuvant (CFA; Difco Laboratories, Detroit, Mich.). Twenty one days later animals were again immunized with antigen in incomplete Freund's adjuvant (FA). Animals were bled and salivated prior to injection, at day 21 and day 42 after the first injection. Sera and clarified salivas were stored at −70° C. prior to assay.

ELISA:

Serum IgG and salivary IgA antibodies were tested by enzyme-linked immunosorbent assay (ELISA). Polystyrene microtiter plates (Flow Laboratories) were coated with 2.5 $\mu$g/ml of each peptide construct or 0.5 $\mu$g/ml of S. sobrinus or S. mutans GTF. Antibody activity was then measured by incubation with 1:400 and 1:4000 dilutions of sera, or 1:4 and 1:8 dilutions of saliva. Plates were then developed for IgG antibody with rabbit anti-rat IgG, followed in sequence by alkaline phosphatase goat anti-rabbit IgG (Biosource Inc.) and p-nitrophenylphosphate (Sigma Chemical Co., St. Louis, Mo.). A mouse monoclonal reagent to rat $\alpha$ chain (Zymed, South San Francisco, Calif.) was used with biotinylated goat anti-mouse IgG (Zymed) and avidin-alkaline phosphatase (Cappel) to reveal levels of salivary IgA antibody to peptides. Reactivity was recorded as absorbance ($A_{405\ nm}$) in a micro plate reader (Biotek Instruments, Winooski, Vt.). Data are reported as ELISA units (EU) which were calculated relative to the levels of appropriate reference sera or salivas from Sprague Dawley rats twice immunized with the respective peptide construct. Dilutions of sera producing an $A_{405\ nm}$ of approximately 1.0 were considered 100 EU for serum IgG antibody measurements. These corresponded to dilutions of 1:51,200, 1:25,000, 1:12,800 or 1:6,400 for serum antibody to S. sobrinus GTF, S. mutans GTF, EAW or HDS constructs, respectively. Dilutions of saliva producing an $A_{405\ nm}$ of approximately 0.8 were considered 100 EU for salivary IgA antibody measurements. These correspond to dilutions of 1:4 for salivary IgA to both EAW and FIDS constructs.

Antibody Inhibition of Glucan Synthesis:

Selected rat sera were evaluated for their ability to inhibit water-soluble glucan synthesis catalyzed by S. mutans GTF, using a filter assay. This GTF preparation contains a mixture of GTFs, including GTF-B which has complete homology with both peptide constructs in the respective region (Table 1). Ten $\mu$l volumes of diluted sera (1:10 dilutions in 0.02 M sodium phosphate buffered saline and 0.2% sodium azide [PBSA], pH 6.5) were preincubated with the GTF for 1 hour at 37° C. in a total volume of 0.04 ml PBSA. The 1.7 mg sucrose and 24 nCi of [$^{14}$C-glucose]-sucrose (approximately 35,000 cpm) were added in 0.2 ml PBA in the absence of primer (Taubman, et al., *Infect. Immun.* 63:3088–3093 (1995)). Incubation proceeded overnight at 37° C. after which water-insoluble glucan was collected on, and water-soluble glucan collected after passage through Whatman GF/F glass fiber filters. Water-insoluble glucan collected on filters was washed and retained radioactivity determined as previously reported (Taubman, et al., *J. Oral Pathol.* 17:466–470 (1988)). Water soluble glucan was precipitated with 70% ethanol and radioactivity determined as previously described (Taubman, et al., *J. Oral Pathol.* 17:466470 (1988)). Under the conditions of this assay, approximately 800 counts per minute (cpm) were incorporated into water-soluble glucan, and 3000 cpm were incorporated into water-insoluble glucan, in the presence of sham immune sera. Percentage inhibition of enzyme activity was calculated using these mean sham incorporation cpm values as the 100% incorporation levels.

RESULTS

Immunogenicity of Peptides:

Antibody levels measured in sera collected 42 days after initial antigen injection are presented in Tables 2 and 3. Results are shown for sera tested at 1:400 dilutions. Serum antibody could be detected 21 days after the initial injection in most HDS and EAW-injected rats. By day 42, all HDS- (Table 2) and EAW- (Table 3) peptide injected rats had high levels of serum IgG antibody to epitope(s) associated with the respective peptide. In fact, serum antibody could be detected at dilutions greater than $10^5$ in some sera from rats injected with HDS and EAW peptide constructs. In contrast, injection with MAC induced IgG antibody that could be detected at 1:400 diluted sera in 4/5 rats, but was absent in 3 of 5 rat sera at a dilutions of 1:1600. No significant reactivity with HDS or EAW was observed with sera from sham, MAC or GTF-injected groups. Also, sera from HDS or EAW-injected rats did not cross react with the heterologous peptide (Tables 2 and 3).

Two immunizations with the HDS and EAW peptide constructs also induced significant levels of salivary IgA antibody that were reactive with the respective peptide in all rats by day 42 (Tables 2 and 3). The HDS peptide construct also induced elevated salivary IgA immune responses in 3/7 HDS-injected rats on day 21 after one immunization, although no antibody to EAW could be detected at this time in EAW-injected rats. Thus, both the EAW and HDS peptide constructs have significant systemic and mucosal immunogenicity when given by the subcutaneous route of injection.

Reactivity with GTF:

All antisera were evaluated by ELISA for IgG antibody reactive with S. mutans GTF preparations. Sera from all rats injected with S. mutans GTF and EAW had elevated levels of IgG antibody to S. mutans GTF at day 21 and day 42 (FIG. 1). Anti-GTF antibody levels in day 42 sera of 2/5 EAW-injected rats were within the range of those of the GTF-injected rats, suggesting that the epitope(s) presented on the EAW-peptide construct is(are) prominent on native GTF. Sera from 6/7 rats injected with the HDS peptide construct demonstrated IgG antibody that reacted with S. mutans GTF on day 42 (FIG. 1). At that time, 5/7 HDS-injected rats showed serum IgG reactivity to GTF within the range of the GTF-injected rats. In contrast, antibody to MAC-injected rats had significantly lower levels of antibody reactive with S. mutans GTF.

Inhibition of GTF Activity:

Sera from sham-, GTFsm-, and peptide construct-injected rats were evaluated for their ability to inhibit the formation of water-soluble and water-insoluble glucan by S. mutans GTF. Sera from many, but not all, EAW, and HDS-injected rats inhibited the ability of S. mutans GTF to synthesize water-soluble glucan (FIG. 2). The level of inhibition of water-soluble glucan formation approached 20% in sera of three rats injected with EAW or HDS peptide constructs. In contrast, no serum from rats injected with the MAC peptide construct inhibited S. mutans GTF water-soluble glucan synthetic activity. Water-insoluble glucan formation by S. mutans GTF was not found to be inhibited by sera from any peptide-injected rat under the conditions of this assay.

TABLE 1

Amino acid sequence homology of MAC, EAW and HDS peptides with S. mutans, S. sobrinus and S. downei GTFs and association with β5 and β7 strand domains

| GTF/peptide (reference) | | Sequence | Homology with Peptide |
|---|---|---|---|
| MAC peptide | | PQWNGESEKFYDDHL (SEQ ID NO. 4) | |
| GTF-B | S. mutans[1] | 342-SAWNSDSERPFDDHL (SEQ ID NO. 5) | 53% |
| GTF-C | S. mutans[2] | 368-SAWNSDSEKPFDDHL (SEQ ID NO. 6) | 67% |
| GTF-D | S. mutans[3] | 354-PNWNSQTESDTSAGE (SEQ ID NO. 7) | 27% |
| GTF-I | S. dawnei[1] | 342-PQWNGESEKPYDDHL (SEQ ID NO. 8) | 100% |
| GTF-S | S. downei[4] | — | 0% |
| GTF2 | S. sobrinus[5] | 336-PQWNGESEKPYDDHL (SEQ ID NO. 9) †# | 100% |
| EAW peptide | | ANDHLSILEAWSDNDTPYLHD (SEQ ID NO. 1) | |
| GTF-B | S. mutans | 480-ANDHLSILEAWSDNDTPYLHD (SEQ ID NO. 1) | 100% |
| GTF-C | S. mutans | 506-ANDHLSILEAWSYNDTPYLHD (SEQ ID NO. 10) | 95% |
| GTF-D | S. mutans | 494-AINHLSILEAWSDNDPQYNKD (SEQ ID NO. 11) | 68% |
| GTF-I | S. downei | 482-ANNHVSIVEAWSDNDTPYLHD (SEQ ID NO. 12) | 90% |
| GTF-S | S. downei | 467-AIDHLSILEAWSGNDNDYVKQ (SEQ ID NO. 13) | 63% |
| GTF2 | S. sobrinus | 476-ANNHVSIVEAWSDNDTPYLHD (SEQ ID NO. 14) ..β5. ‡ †◻ | 84% |
| HDS peptide | | VPSYSFIRAHDSEVQDLIA (SEQ ID NO. 2) | |
| GTF-B | S. mutans | 549-VPSYSFIRAHDSEVQDLIA (SEQ ID NO. 2) | 100% |
| GTF-C | S. mutans | 575-VPSYSFIRAHDSEVQDLIRNII (SEQ ID NO. 15) | 95% |
| GTF-D | S. mutans | 571-MANYIFIRAHDSEVQTVAKII (SEQ ID NO. 16) | 63% |

TABLE 1-continued

Amino acid sequence homology of MAC, EAW and HDS peptides with S. mutans, S. sobrinus and S. downei GTFs and association with β5 and β7 strand domains

| GTF/peptide (reference) | | Sequence | Homology with Peptide |
|---|---|---|---|
| GTF-I | S. downei | 551-VPSYSFARAHDSEVQDLIRDII (SEQ ID NO. 17) | 84% |
| GTF-S | S. downei | 534-VPNYVFIRAHDSEVQTRIAKII (SEQ ID NO. 18) | 74% |
| GTF-2 | S. sobrinus | 545-VPSYSFARAHDSEVQDIIRDII (SEQ ID NO. 19) | 84% |

†Glutamic and aspartic acids at these positions are catalytic in alpha amylases (Matsuura, et al., J. Biochem. 95:697–702 (1984); Tsumori, et al., J.Bacterialo 179:3391–3396 (1997)); modification of these amino acids in GTF leads to loss of activity (Devulapalle, et al., Protein Science 6:2489–2493 (1997); Tsumori, et al., Infect. Immun. 179:3391–3396 (1997)).
‡Histidine stabilizes transition states at this position in alpha amylases (Matsuura, et al., J. Biochem. 95:697–702 (1984); Sogaard, et al., J. Biol. Chem. 268:22480–22484 (1993)); modification of this histidine in GTF leads to loss of activity (Tsumori, et al., Infect. Immun. 179:3391–3396 (1997)).
Tryptophane is highly conserved at this position in GTF; activity is lost when mutated (Tsumori, et al., Infect. Immun. 179:3391–3396 (1997)).
◻Glucan product type changed when aspartic acid at this position in GTF is mutated (Shimamura, et al., J. Bact., 176:4845–4850 (1994)).
[1]Ferretti, et al., J. Bacteriol. 169:4271–4278 (1987)
[2]Shiroza, et al., J. Bacertiol. 169:4263–4270 (1987)
[3]Honda, et al., J. Gen. Microbiol. 136:2099–2105
[4]Gilmore, et al., Infect. Immun. 58:2452–2458 (1990)
[5]Abo, et al., J. Bacterol. 173:989–996 (1991)

TABLE 2

Serum and salivary immune responses to HDS after subcutaneous injection with MAC, EAW, or HDS peptide constructs or S. mutans GTF (n = 4–7 rats/group).

| | Mean Serum IgG EU ± SE | | | Mean Salivary IgA EU ± SE | | |
|---|---|---|---|---|---|---|
| Group | pre | day 42 | range | pre | day 42 | range |
| Sham | 0 ± 0 | 0 ± 0 | 0 | 1 ± 1 | 0 ± 0 | 0 |
| MAC | 0 ± 0 | 0 ± 0 | 0 | 0 ± 0 | 1 ± 1 | 0 |
| EAW | ND* | 0 ± 0 | | ND | ND | |
| HDS | 0 ± 0 | 118 ± 18 | 99–155 | 1 ± 1 | 142 ± 36 | 16–206 |
| GTFsm | 0 ± 0 | 0 ± 0 | 0 | 0 ± 0 | 1 ± 1 | 0 |

*ND = not done

TABLE 3

Serum and salivary immune responses to EAW after subcutaneous injection with MAC, EAW, or HDS peptide constructs or S. mutans GTF (n = 4–7 rats/group).

| Injected | Mean Serum IgG EU ± SE | | | Mean Salivary IgA EU ± SE | | |
|---|---|---|---|---|---|---|
| Group | pre | day 42 | range | pre | day 42 | range |
| Sham | 0 ± 0 | 0 ± 0 | 0 | 0 ± 0 | 0 ± 0 | 0 |
| MAC | ND* | 0 ± 0 | 0 | ND | ND | — |
| EAW | 0 ± 0 | 117 ± 40 | 105–126 | 1 ± 1 | 53 ± 19 | 14–78 |
| HDS | ND | 0 ± | ND | ND | — | |
| GTFsm | 0 ± 0 | 2 ± 2 | 0 | 0 ± 0 | 1 ± 1 | 0 |

Equivalents

Those skilled in the art will recognize or be able to ascertain using no more than routine experimentation, many equivalents to the specific embodiments of the invention described herein. Such equivalents are intended to be encompassed in the scope of the following claims.

We claim:

1. An immunogenic composition comprising at least one peptide consisting essentially of SEQ ID NO: 3.

2. An immunogenic composition comprising a radially branched macromolecular structure, said structure comprising a peptidyl core matrix comprising at least 3 amino acids selected from the group consisting of a lysine, arginine, and histidine residue; and at least 4 glucosyltransferase polyepotides, each polypeptide of which is covalently attached to and radially branched about said peptidyl core amino acid, wherein said glucosyltransferase polypeptides are selected from the group consisting of SEQ ID NO: 1; SEQ ID NO: 2; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; and SEQ ID NO: 19.

3. An immunogenic composition comprising at least one peptide which is an amino acid sequence subunit of glucosyltransferase of 15–22 amino acids in length comprising an amino acid sequence selected from the group consisting of: SEQ ID NO: 1; SEQ ID NO: 2; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; and SEQ ID NO: 19.

4. The immunogenic composition of claim 3, wherein said amino acid sequence is SEQ ID NO: 1.

5. The immunogenic composition of claim 3, wherein said amino acid sequence is SEQ ID NO: 2.

6. The immunogenic composition of claim 3, wherein said amino acid sequence is SEQ ID NO: 10.

7. The immunogenic composition of claim 3, wherein said amino acid sequence is SEQ ID NO: 11.

8. The immunogenic composition of claim 3, wherein said amino acid sequence is SEQ ID NO: 12.

9. The immunogenic composition of claim 3, wherein said amino acid sequence is SEQ ID NO: 13.

10. The immunogenic composition of claim 3, wherein said amino acid sequence is SEQ ID NO: 14.

11. The immunogenic composition of claim 3, wherein said amino acid sequence is SEQ ID NO: 15.

12. The immunogenic composition of claim 3, wherein said amino acid sequence is SEQ ID NO: 16.

13. The immunogenic composition of claim 3, wherein said amino acid sequence is SEQ ID NO: 17.

14. The immunogenic composition of claim 3, wherein said amino acid sequence is SEQ ID NO: 18.

15. The immunogenic composition of claim 3, wherein said amino acid sequence is SEQ ID NO: 19.

16. The An immunogenic composition comprising a macromolecular structure, said structure comprising a peptidyl core matrix comprising at least one amino acid selected from the group consisting of a lysine, arginine, and histidine residue; and at least two glucosyltransferase polypeptides covalently attached to said peptidyl core amino acid, wherein said glucosyltransferase polypeptides are selected from the group consisting of SEQ ID NO: 1; SEQ ID NO: 2; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; and SEQ ID NO: 19.

17. The immunogenic composition of claim 16, wherein said at least two peptides is an amino acid sequence of SEQ ID NO: 1 and an amino acid sequence selected from the group consisting of SEQ ID NOs: 1, 2, 10, 11, 12, 13, 14, 15, 16, 17, 18, and 19.

18. The immunogenic composition of claim 16, wherein said at least two peptides is an amino acid sequence of SEQ ID NO: 2 and an amino acid sequence selected from the group consisting of SEQ ID NOs: 1, 2, 10, 11, 12, 13, 14, 15, 16, 17, 18, and 19.

19. The immunogenic composition of claim 16, wherein said at least two peptides is an amino acid sequence of SEQ ID NO: 10 and an amino acid sequence selected from the group consisting of SEQ ID NOs: 1, 2, 10, 11, 12, 13, 14, 15, 16, 17, 18, and 19.

20. The immunogenic composition of claim 16, wherein said at least two peptides is an amino acid sequence of SEQ ID NO: 11 and an amino acid sequence selected from the group consisting of SEQ ID NOs: 1, 2, 10, 11, 12, 13, 14, 15, 16, 17, 18, and 19.

21. The immunogenic composition of claim 16, wherein said at least two peptides is an amino acid sequence of SEQ ID NO: 12 and an amino acid sequence selected from the group consisting of SEQ ID NOs: 1, 2, 10, 11, 12, 13, 14, 15, 16, 17, 18, and 19.

22. The immunogenic composition of claim 16, wherein said at least two peptides is an amino acid sequence of SEQ ID NO: 13 and an amino acid sequence selected from the group consisting of SEQ ID NOs: 1, 2, 10, 11, 12, 13, 14, 15, 16, 17, 18, and 19.

23. The immunogenic composition of claim 16, wherein said at least two peptides is an amino acid sequence of SEQ ID NO: 14 and an amino acid sequence selected from the group consisting of SEQ ID NOs: 1, 2, 10, 11, 12, 13, 14, 15, 16, 17, 18, and 19.

24. The immunogenic composition of claim 16, wherein said at least two peptides is an amino acid sequence of SEQ ID NO: 15 and an amino acid sequence selected from the group consisting of SEQ ID NOs: 1, 2, 10, 11, 12, 13, 14, 15, 16, 17, 18, and 19.

25. The immunogenic composition of claim 16, wherein said at least two peptides is an amino acid sequence of SEQ ID NO: 16 and an amino acid sequence selected from the group consisting of SEQ ID NOs: 1, 2, 10, 11, 12, 13, 14, 15, 16, 17, 18, and 19.

26. The immunogenic composition of claim 16, wherein said at least two peptides is an amino acid sequence of SEQ ID NO: 17 and an amino acid sequence selected from the group consisting of SEQ ID NOs: 1, 2, 10, 11, 12, 13, 14, 15, 16, 17, 18, and 19.

27. The immunogenic composition of claim 16, wherein said at least two peptides is an amino acid sequence of SEQ ID NO: 18 and an amino acid sequence selected from the group consisting of SEQ ID NOs: 1, 2, 10, 11, 12, 13, 14, 15, 16, 17, 18, and 19.

28. The immunogenic composition of claim 16, wherein said at least two peptides is an amino acid sequence of SEQ ID NO: 19 and an amino acid sequence selected from the group consisting of SEQ ID NOs: 1, 2, 10, 11, 12, 13, 14, 15, 16, 17, 18, and 19.

\* \* \* \* \*